United States Patent [19]

Tömösközi et al.

[11] 4,126,622
[45] Nov. 21, 1978

[54] BICYCLIC LACTONE DERIVATIVES EMPLOYED AS INTERMEDIATES IN THE SYNTHESIS OF PROSTAGLANDINES

[75] Inventors: István Tömösközi; Gábor Kovács, both of Budapest; István Székely, Szentendre; Vilmos Simonidesz, Budapest; Marianna Lovász née Gáspár, Budapest; Borbála Keresztes née Ördög, Budapest; Julia Remport née Rádóczi, Budapest; István Stadler, Budapest; Zsuzsa Visky née Gombos, Budapest; Csaba Szántay, Budapest, all of Hungary

[73] Assignee: Chinoin Gyogyszer es Vegyeszeti Termekek Gyara RT, Budapest, Hungary

[21] Appl. No.: 770,998

[22] Filed: Feb. 22, 1977

[30] Foreign Application Priority Data

Feb. 20, 1976 [HU] Hungary .............................. CI 1644

[51] Int. Cl.$^2$ .......................................... C07D 319/08
[52] U.S. Cl. ............................ 260/340.3; 260/343.3 P
[58] Field of Search ....................................... 260/340.3

[56] References Cited
U.S. PATENT DOCUMENTS 3,778,461  12/1973  Brown et al. ..................... 260/340.3

Primary Examiner—Ethel G. Love
Attorney, Agent, or Firm—Karl F. Ross

[57] ABSTRACT

A compound of the formula is disclosed.

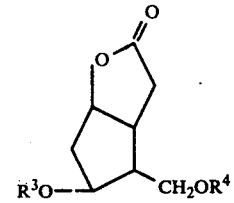

wherein $R^3$ and $R^4$ are the same or different and are each hydrogen, lower alkanoyl, lower alkanoyl substituted by 1, 2, or 3 halogen atoms, or $R^3$ and $R^4$ together form an

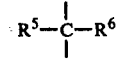

group in which $R^5$ and $R^6$ are the same or different and are each hydrogen, alkyl or aryl as well as a process for the preparation thereof.

4 Claims, No Drawings

BICYCLIC LACTONE DERIVATIVES EMPLOYED AS INTERMEDIATES IN THE SYNTHESIS OF PROSTAGLANDINES

This invention relates to certain optically active or racemic lactone diol derivatives. Such compounds are useful as intermediates in the Corey prostaglandine synthesis.

The natural prostaglandines constitute a group having outstanding biological activity of the endogenous tissue-hormones. Starting from the late sixties when the natural prostaglandines were isolated and their structure was evaluated, intense research work has been going on to perfect methods for synthesizing those compounds as well as to prepare compounds of analogous structure — the so called prostanoides — in order to evaluate their harmacological activity [J.A.C.S., 93, 4326 (1971)]. The nomenclature and biological activity of the prostaglandines and the methods for the synthesis thereof are disclosed in numerous monograp and other publications (e.g. Arzneimittel Forsch. 25, 135 (1975)).

As to the solution of stereochemical problems, the synthesis described in J.A.C.S., 91 5675 (1969), ibid. 92, 397 (1970), and ibid 933, 1490, (1971) takes an outstanding place among the various total synthesis methods, and fulfills also the requirements of industrial realization. The end product of this synthesis is $PGF_{2\alpha}$, which can be easily transformed into other pharmaceutically important natural prostaglandines, e.g., into $PGE_1$, $PGE_2$, $PGF_{1\alpha}$ or $PGF_{1\beta}$.

During the above synthesis the Wittig reaction is employed for the stereoselective formation of double bonds. Use is made of the ability arising from the structure of the prostaglandines to form a trans-double bond with the necessary phosphonate (stabilized ylide) in the side-chain containing an allyl alcohol moiety, and at the same time to produce in the other side-chain with the phosphorane generated from the 4-carboxybutyl-triphenylphosphonium bromide (reactive ylide) a cis-olefine.

The key intermediate of the synthesis is the so called "Corey aldehyde" having four centers of asymmetry with the same absolute and relative configuration as in $PGF_{2\alpha}$. According to this synthesis the aldehyde of the formula III

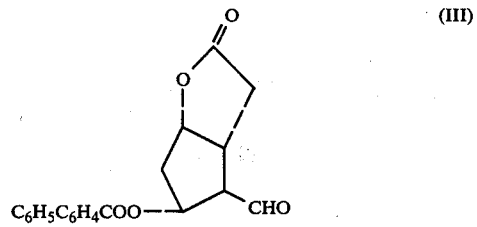

is prepared by oxidizing the alcohol of the formula IV, as it is illustrated on the following scheme:

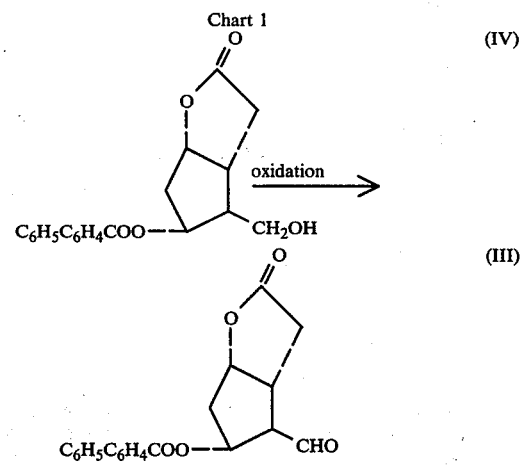

The stereochemically controlled reaction for the preparation of the alcohol of the formula IV may be depicted by the following scheme:

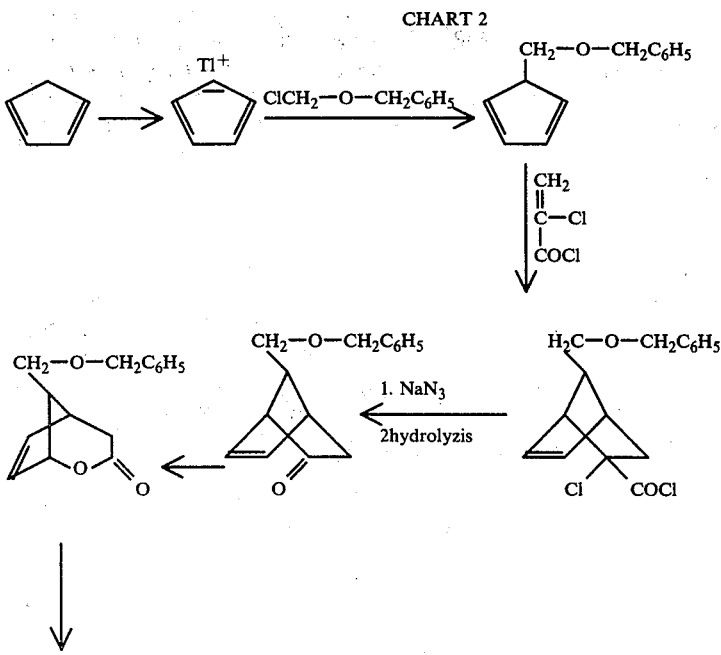

CHART 2 -continued

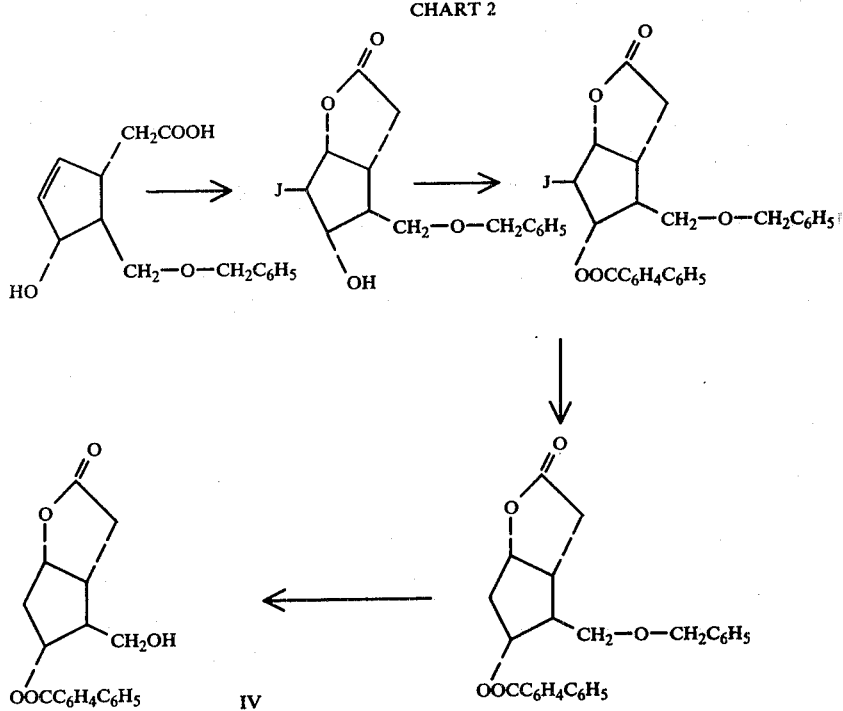

A large number of modified versions of this synthesis has been published in various publications and patents [for example J.C.S. Chem. Comm. 151 (1974); ibid 642 (1974); ibid 39 (1975); J.A.C.S., 96, 5261 (1974)].

However, none of these variants modifies the sequence of reactions resulting in the formation of the suitable stereoisomer [6a(S), 3a(R), 4(S), 5(R)] of the hexahydro-2(H)-cyclopentano[b]furane derivative of the formula IV. In all cases the following reactions are used in the following order: bicyclo[2,2,1]heptene-on derivatives prepared by a stereochemically controlled Diels-Alder reaction are subjected to a regiospecific Baeyer-Villinger oxidation, the obtained δ-lactone is hydrolyzed to a hydroxy-acid which is then subjected to a iodine-lactone forming reaction, when the above compound of the formula IV is obtained.

However, the synthesis described in Chart 2 has a number of disadvantages. The preparation of the compounds of the formula IV in this manner is extremely complicated and expensive due to the high number of the reaction steps, and to the fact that the reagents are difficult to obtain (for example α-chloro acrylic acid chloride and chloromethyl benzylester may be prepared by a synthesis having more reaction steps) and are toxical (e.g. thallium compounds, tributylone hydride).

The intermediate of the formula V which may replace the compound of the formula III in the Corey synthesis can be prepared by the method described on Chart 3. [J.A.C.S., 95, 6853 (1973)].

CHART 3

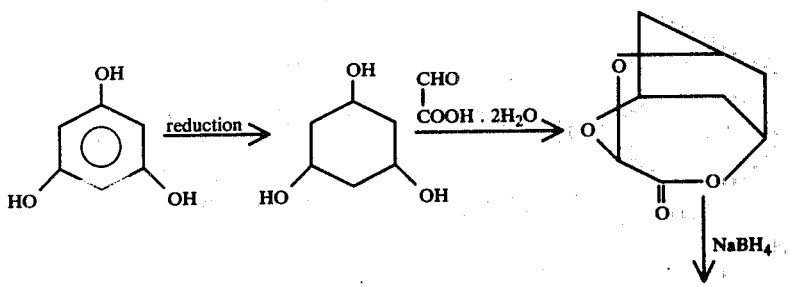

-continued
CHART 3

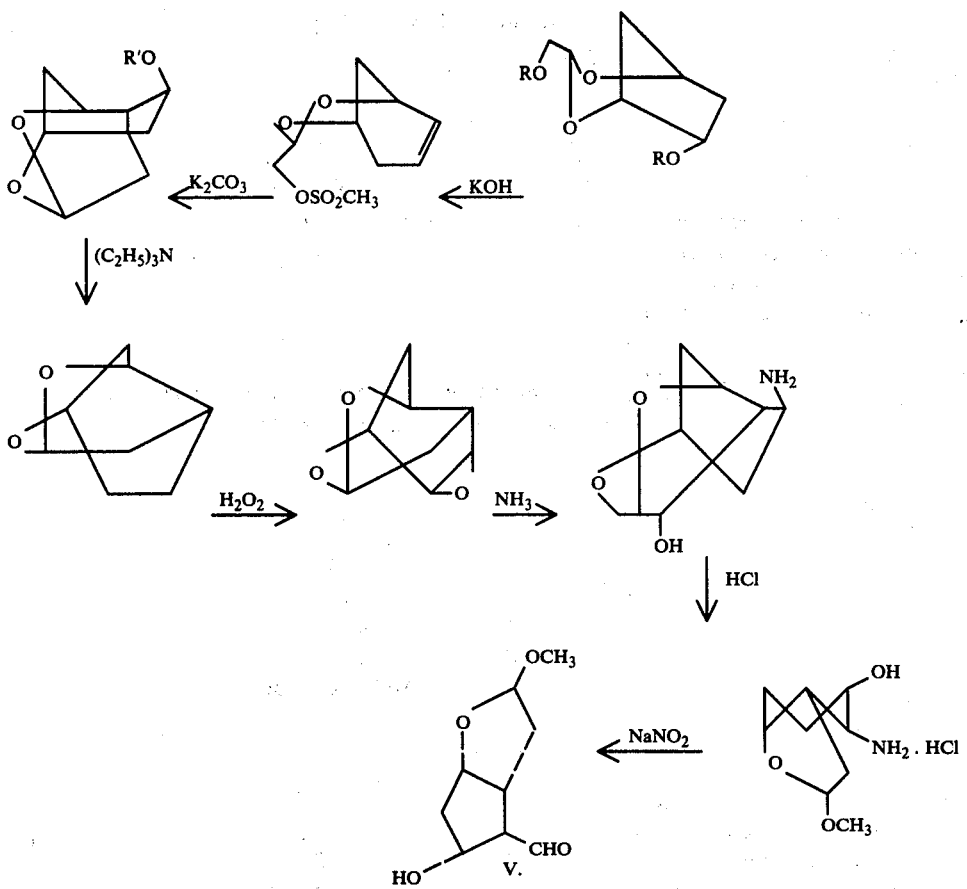

It can be seen however, that also this synthesis consists of numerous reaction steps, and the isomers obtained by the epoxidation should be separated on a chromatographic column, which makes the process complicated and expensive.

We have surprisingly found that the compounds of the formula I

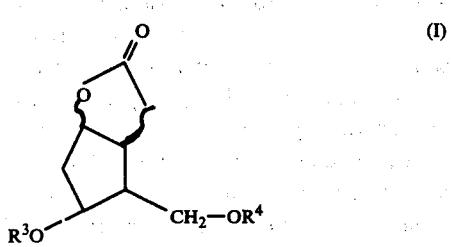

wherein $R^3$ and $R^4$ are identical or different and stand for a hydrogen or a lower alkanoyl optionally substituted by one, two or three halogen(s) or together form a

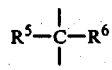

group, wherein $R^5$ and $R^6$ are identical or different and stand for a hydrogen, alkyl or aryl, can be prepared in a much simpler way according to the method of this invention.

Our invention resides in the realization that the Prins reaction has a stereospecific trans-addition character [Chem. Rews. 51, 505 (1952)]. The stereochemistry and the reaction mechanism of the Prins reaction, which consists in the addition reaction of formaldehyde on olefines in the presence of an acid catalyst, has already been evaluated to large extend [Bull. Chem. Soc. Chem. France, 357 (1952)].

Although, the Prins reaction is not necessarily regiospecific, generally it proceeds stereospecifically. The acid in the reaction medium performs a double role: reacting with the monomer formaldehyde it produces the methylol cation ($^+CH_3OH$) which attacks in the first reaction step the $\pi$-electron system of the double bond, and on the other hand it acts as a catalyst in the depolymerisating reaction of the formaldehyde polymer (paraformaldehyde, trioxymethylene). The acid can be sulphuric acid, phosphoric acid, borontrifluoride etherate etc.

The end products of the Prins reaction depend to a large extent on the employed solvent (acetic acid, water, aprotic solvent). In the generally used acetic acid and water solvents the main product is the hydroxymethyl alcohol derived from the applied olefine, and the acetylated as well as 1,3-dioxane-derivatives thereof. The latter product is obtained by means of formaldehyde.

In our process the known 3,3a,6,6a-tetrahydro-2H-cyclopentano[b]furane-2-on of the formula II

(II)

(the other conventional name of the compound is: cis-2-oxa-bicyclo[3,3,0]oct-6-ene-3-on) and its optically active forms, the (−)-[6a(S), 3a(R)]- and the (+)-[6a(R), 3a(S)]-isomers, that is the (−) and (+) compound of the formula II are used as the olefin component when carrying out the Prins reaction. The above compound is disclosed for example in the Tetr. Lett. 307–310, 1970.

The compound of the formula II can be prepared in one reaction step by the addition of mono- or dichloroethene on cyclopentadiene, or by oxidizing the known (3,2,0)hept-5-ene-2-on of the formula VI

(VI)

with hydrogen peroxide. The resolution of the compound of the formula II with (+)-α-methyl-benzylamine has also been described in the literature (J.A.C.S., 95, 6832 /973/). For the preparation of the enantiomers of the compound of the formula II an asymmetric synthesis comprising three steps is described in J.A.C.S. 95, 7171 /1973/. The compound of the formula II in its racemic and optically active (+) and (−) forms

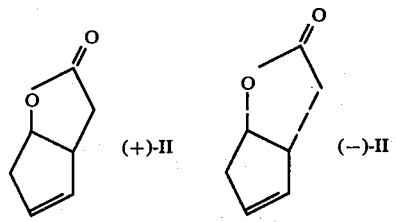

as well has played a deciding role in the synthesis of various prostanoides and prostanoide intermediates, respectively [Tetr. Lett. 4753 (1971); ibid. 3091 (1973); J.A.C.S. 95, 6832 (1973); Tetr. Lett. 2439 (1974)]. For transformation of the above compound into natural prostaglandines, however, only a very complicated reaction has been described based on the conjugated addition of lithium dialkenyl cuprates or mixed cuprates, which could be prepared only under exact and complicated reaction conditions and after some subsequent chromatographic purification steps of high level.

As a result of our investigations we found that the reaction of the racemic or optically active compound of the formula II with formaldehyde in the presence of sulphuric acid catalyst (Prins reaction) is regio- as well as stereospecific, when carried out in an acetic acid medium and as a main product the compound of the formula Ic

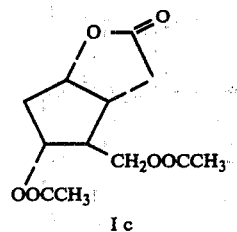

Ic is obtained with an excellent yield, while the quantity of the compounds of the formula Ia

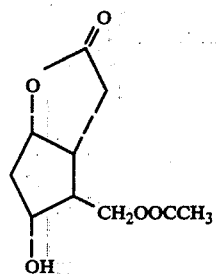

(Ia)

and Ib

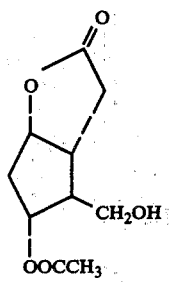

(Ib)

is between 5 and 10% depending on the reaction conditions. Thus the formation of the partially acetylated compounds of the formula Ia and Ib is the function of the temperature of the quality of the formaldehyde, paraformaldehyde and trioxymethylene applied, and the water content of the acetic acid solvent. These partially acetylated products can be eliminated only by a subsequent in situ acetylation carried out for example with acetic anhydride.

As a consequence of the mechanism of Prins reaction the main product of the reaction, the compound of the formula Ia is susceptible to a proton catalysed acryl migrating reaction, when the compound of the formula Ib is obtained. Both of the partially acetylated lactone diols can be acetylated in the presence of a proton donor catalyst, but the water formed during the esterification remains in the system, and thus an equilibrium mixture is obtained with a composition depending on the reaction conditions.

Chart 4

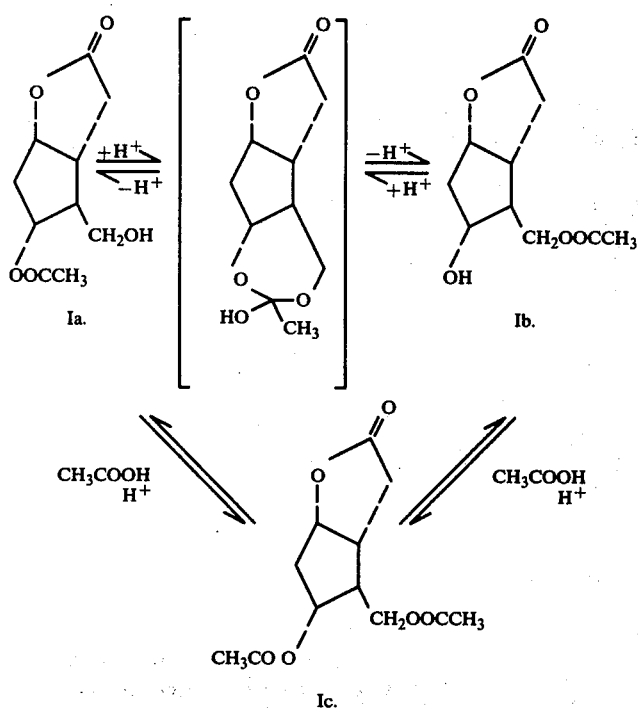

The rate of the aceylation of the compounds of the formula Ia and Ib, respectively is different. As it is expected, the primary hydroxyl can be acetylated at a several times higher rate than the secondary hydroxyl. The rate of the acyl migration in the secondary → primary direction is higher then in the contrary one.

The formation of the partially acetylated products does not mean any disadvantage when the acetylated products (s) is (are) subjected to a hydrolysis catalyzed by an alkali alkoxide alkali carbonate or by an acid, or to alcoholysis. The alcoholysis can be accomplished in the presence of atmost 10 to 20 mole percent of an acid catalyst. The alcoholysis catalyzed by an acid can be completed in the presence of a catalytic amount of a mineral acid or an arylsulphonic acid by distilling off the resulting alkyl acetate. The alcoholysis is carried out preferably with methanol, since the obtained methylacetate has an advantageously low boiling point and thus is easy to distill off. By the acid or alkaline hydrolysis of the product mixture obtained by the Prins reaction the lactone diol of the formula VII is prepared.

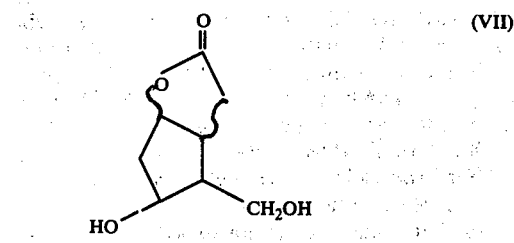

(VII)

The compound of the formula VII is known to the art (J.A.C.S., 93, 1491 (1971)). In the cited reference another method for the preparation of the compound, its melting point and optical rotatory power are described. The physical characteristics of the compound of the formula VII prepared according to our method are identical with those published in the literature.

When the optically active compound of the formula VII is prepared by acid catalyzed methanolysis, the crystalline row product remained after evaporating the solvent can be subjected to the selective acylation into the compound of the formula IV or to the selective oxidation into the compound of the formula V (U.S. Pat. application No. 770,997) without any further purification.

The alcoholysis catalyzed by alkali alkoxise or alkali carbonate can be performed at room temperature, but in this case it is expedient to eliminate the salt resulted by the neutralization prior to evaporating the solvent, for example by passing the mixture through a silica gel column.

The compound of the formula VII can be recrystallized from ethyl acetate, ethyl acetate/hexane or acetonitrile/ether. After recrystallization the compound of the formula VII is obtained at a yield of 80 to 90% (calculated on the starting compound of the formula II).

The primary product mixture obtained by the Prins reaction can be transformed by in situ acetylation into the lactone diol diacetate of the formula Ic almost quantitatively. Thus the compound of the formula Ic, which is a new compound, can be obtained with a yield of 90 to 95% when starting from the compound of the formula II.

In order to prove the absolute and relative configuration of the compound of the formula Ic prepared by the Prins reaction, we prepared the compound also according to the reaction depicted in the Chart 5.

Chart 5

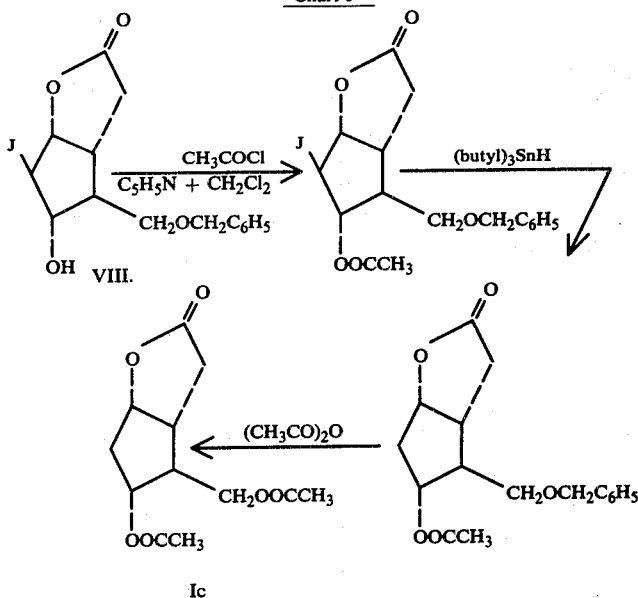

We started from the iodine lactone of the formula VIII known in the Corey synthesis, and subjected the compound to a series of transformations influencing none of the chiral centers. The thus obtained compound including its optical rotatory power was identical with the left-hand rotating compound of the formula Ic prepared from the (—) compound of the formula II by the Prins reaction.

The compound of the formula Ia can be prepared by the partial solvolitic deacetylation of the lactone diol diacetate of the formula Ic. The compound of the formula Ia can be employed in the Corey synthesis in the same way as the compound of the formula IV. We found that this desacetylation can not be absolutely selective due to the acyl migration described above. The quantity of the compounds of the formula Ib and Ic in the reaction mixture, however, can be minimized by finding the optimum proton, alkoxide and carbonate concentrations, reaction time and above all reaction temperature. After the partial deacetylation the compound of the formula Ia can be separated from the compounds of the formula Ib and Ic by column chromatography. The separation is carried out on a silicagel column by the gradient eluation technique using ethylacetate/methanol mixture of increasing methanol concentration as an eluent. The first fractions contain first of all the compound of the formula Ib, the followings the compound of the formula Ia, and then the compound of the formula Id is obtained.

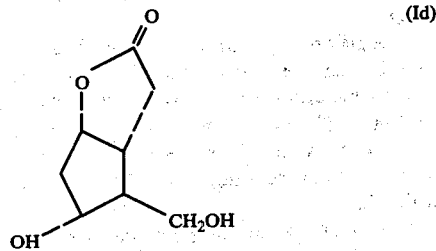

When reacting the obtained lactone diol of the formula Id with excess of paraformaldehyde in benzene, in the presence of a small amount of phosphorous oxychloride catalyst, in a closed system, at room temperature for some days, a 1,3-dioxane-derivative of the formula IX

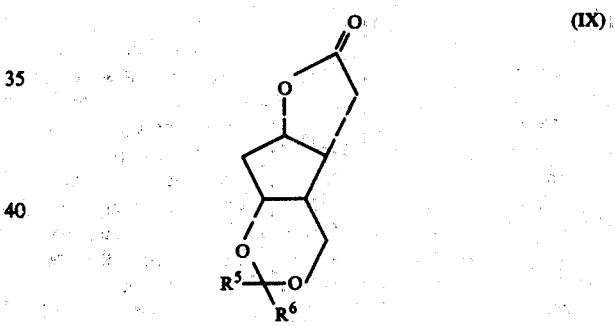

is obtained, wherein $R^5$ and $R^6$ is hydrogen. The traces of this product can be detected also among the products of the Prins reaction. The above-outlined reaction leading to the formation of a cyclic acetal can be performed also with other aldehydes and ketones. This when replacing formaldehyde by benzaldehyde or acetone, respectively, a compound of the formula IX is obtained, in which $R^5$ is phenyl and $R^6$ is hydrogen or $R^5$ and $R^6$ stand for a methyl each. The thus obtained compounds of the formula IX are useful intermediates, which contain the two hydroxyls of the compound of the formula Id in a protected form. The protecting cyclic acetal, however, can be easily removed in a mild acid medium.

In the Prins reaction performed with the compound of the formula II the acetic acid can be replaced also by other lower alkane carboxylic acids. The reaction can be carried out also with lower alkane carboxylic acids containing one, two or three halogens, when those compounds of the formula I are obtained, in which $R^3$ and $R^4$ represent a hydrogen and/or an appropriate acyl group.

The reaction can be accomplished also in the absence of an acid. In this case the concentrated sulphuric acid catalyst and then the compound of the formula II are added to an aqueous formaldehyde solution.

The closed system is then kept at 70° C for 70 to 80 hours. The main product is the compound of the formula Id, but a compound of the formula IX, in which $R^5$ and $R^6$ are hydrogen is also obtained in a small amount. The compound of the formula Id can be isolated from the mixture by chromatography. The following examples are for illustration only.

EXAMPLE 1

The addition of formaldehyde on (−)-3,3aβ,6,6aβ-tetrahydro-2H-cyclopenteno[b]furane-2-on In a sealable glass tube or in a flask equipped with a glass stoper 2.1 g. of paraformaldehyde (polyoxymethylene) are suspended in 15 ml. of glacial acetic acid and 1 g. of concentrated sulphuric acid is added dropwise, with stirring, at room temperature. After a short stirring the 50 to 70 percent of formaldehyde polymer dissolves (the depolymerization can be completed by keeping the mixture at 50° to 60° C for 30 to 40 minutes). Thereafter the solution of 2.3 g. (18.5mmoles) of (−)-3,3aβ,6,6aβ-tetrahydro-2H-cyclopenteno[b]furane-2-one [(−) compound of the formula II] in 18 ml. of glacial acetic acid is added to the above solution at 20° to 25° C, dropwise, with stirring. The addition is accomplished in 5 to 10 minutes. The tube or flask is closed and the temperature is increased up to 70° C in 1 to 3 hours. The mixture is stirred at this temperature for 24 to 30 hours. The temperature is then increased to 80° C and the reaction mixture is stirred at this temperature for 20 to 24 hours, when the reaction mixture shows a pale brownish color. Upon cooling the mixture is acidified and 3 g. of dry sodium acetate are added, then the most of the resulted acetic acid is evaporated in vacuo (15 torr, 40° to 50° C). The residue is dissolved in ethyl acetate (20 to 30 ml.) and washed to neutral with several portions of saturated sodium carbonate solution. The aqueous washing is extracted with 3 × 15 ml. of ethylacetate. The combined ethylacetate solutions are washed with 2 × 5 ml. of brine, dried over magnesium sulphate, and the solvent is removed. 4.5 to 4.8 g. of yellowish-brown oil are obtained. According to the t.l.c. measurements 90% of the obtained product is the lactone diol diacetate of the formula Ic.

EXAMPLE 2

(−)-3,3a,β,4,5,6,6aβ-hexahydro-4β-acetoxymethyl-5α-acetoxy-2H-cyclopenta[b]furane-2-on (compound of the formula Ic)

The Prins reaction is carried out as described in Example 1, with the only difference that after opening the flask and adding the sodium acetate only half of the acetic acid is evaporated, then 2 to 3 ml. of acetic anhydride are added to the reaction mixture, which is then stirred at 40° to 50° C for 2 hours, and evaporated. The residue is worked up according to the Example 1. Eluating the obtained compound of the formula Ic on a silicagel column (200 to 250 g) with a 1:1 mixture of dichloromethane and ethyl acetate 3.8 to 4 g. of a product having the following physical characteristics are obtained:

$[\alpha]_D^{25} = -57.6° \pm 0.5°$ (c = 0.93, chloroform)

$R_f = 0.53$ (on a GF$_{254}$ "Kieselgel nach Stahl" plate, with ethyl acetate)

$R_f = 0.38$ (on the above plate with 1:1 mixture of benzene and ethyl acetate)

$R_f = 0.17$ (on the above plate, with a 3:1 mixture of benzene and ethyl acetate)

$R_f = 0.71$ (on the above plate, with 6:1 mixture of ethyl acetate and methanol) IR ($\nu$max) = 2950, 1770, 1740, 1360, 1230, 1160, 1060 and 1030 cm$^{-1}$.

NMR (C$^{13}$) : In the brackets the results of the off-resonance and the assignments of the structural elements are given.

176.75 (—C̦=O, lactone), 171.15 (—COO—), 170.80 (—COO—), 84.01 (d, —C̦H—O—), 76.95 (d, —C̦H—O—), 63.96 (t, —CH$_2$—OOC—CH$_3$), 51.35 (d, —C̦H—), 40.57 (d, —C̦H—), 38.10 (t, —CH$_2$—), 35.74 (t, —CH$_2$—), 21.05 (q, —CH$_3$) and 20.79 (q, —CH$_3$).

EXAMPLE 3

(−)-3,3aβ,4,5,6,6aβ-hexahydro-4β-hydroxymethyl-5α-hydroxy-2H-cyclopenta[b]furane-2-on (compound of the formula Id)

To the solution of 786 mg. (3 mmoles) of lactone diol diacetate of the formula Ic in 15 ml. of methanol 5 ml. of 0.6 M solution of sodiummethoxide in methanol are added at room temperature. The reaction is completed in 45 to 50 minutes. According to the t.l.c. measurements the solution contains only the named compound. Thereafter 0.3 to 0.5 ml. of acetic acid are added to the reaction mixture drop-wise, with stirring and the methanol is removed by evaporation in vacuo. The residue is dissolved in 10 ml of a 4:1 mixture of ethyl acetate and methanol and the solution is passed through a column made of 12 to 15 g. of silica gel. The column is washed with 80 to 100 ml. of a 4:1 ethyl acetate/methanol mixture. If the lactone diol diacetate contained also the traces of the unsaturated lactone of the formula II remained from the Prins, reaction, the first 1 to 25 ml. of the eluate are collected separately. The following 35 to 80 ml. of eluate contain the chemically pure compound of the formula Id. Evaporating this fraction, 4400 to b 500 ml. of product are obtained. Before a possible further purification the product is preferably dissolved in a small amount of acetonitrile and diluted with ether until slight turbidity. The pure product crystallizes in well-shaped crystals when kept in a refrigerator. Physical characteristics:

Melting point: 117.5° to 118.5° C $[\alpha]_D^{25} = -43.4° \pm 0.5°$ (c = 1.4, methanol).

$R_f = 0.1$ (on a GF$_{254}$ "Kieselgel nach Stahl" plate, with ethyl acetate)

$R_f = 0.35$ (on the above plate but with a 6:1 mixture of ethyl acetate and methanol)

IR (max) = 3350, 2900, 1755, 1170, 1070 and 1030 cm$^{-1}$.

The product proved to be identical with an authentic sample prepared in an other way.

EXAMPLE 4

(−)-3,3aβ,4,5,6,6aβ-hexyahydro-4β-hydroxymethyl-5α-hydroxy-2H-cyclopenta[b]furane-2-on (compound of the formula ID)

To the solution of 910 mg. (3.58 mmoles) of lactone diol diacetate of the formula Ic in 15 ml. of methanol the solution of 50 mg. of p-toluene-sulphonic acid in 3 ml. of methanol is added and the reaction mixture is stirred in a flask equipped with a distillation condenser in a water bath at 68° to 72° C, distilling off the formed methyl acetate. The reaction is completed in about 8 to 10 hours after distilling off about 5 to 6 ml. of a methyl acetate/methanol mixture. Increasing the temperature of the water bath of a further 5 to 6 ml. portion of methanol is distilled off, and the residue is eliminated by aseotropic distillation with benzene (boiling point of the aseotropic mixture: 56° C). The benzene is evaporated in vacuo and the product is purified by column chromatography as in the previous example. 570 to 580 mg. (93 to 95%) of the named compound are obtained. The physical characteristics of the obtained product are identical with the those of the compound of the Example 3.

EXAMPLE 5

(−)-3,3aβ,4,5,6,6aβ-hexahydro-4β-hydroxymethyl-5α-acetoxy-2H-cyclopenta[b]furane-2-on (compound of the formula Ia)

To the solution of 600 ml. (2.36 mmoles) of lactone diol diacetate of the formula Ic in 15 ml. of methanol the solution of 40 mg. of p-toluene-sulphonic acid in 3 ml. of methanol is added and the reaction mixture is stirred at room temperature for 8 to 10 hours. The reaction is controlled by t.l.c.

The $R_f$ values of the main products in the mixture detected on a $CF_{254}$ "Kiselgel nach Stahl" plate are the followings:

| Formula | Ethyl acetate | 6:1 mixture of ethyl acetate and methanol |
|---|---|---|
| Ia | 0.26 | 0.49 |
| Ib | 0.42 | 0.61 |
| Ic | 0.53 | 0.71 |
| Id | 0.10 | 0.35 |

After the reaction is completed the mixture is worked up as described in Example 4. The obtained pale yellow oil is subjected to chromatography on a silica gel column of 50 to 100-times volume using an ethyl acetate/methanol mixture as eluent, gradually increasing the methanol concentration from the ratio of 8:1 up to 3:1. The fractions are subjected to t.l.c. measurements and the fractions containing the same products are combined and evaporated. Thus 310 mg (62%) of lactone diol monoacetate of the formula Ia are obtained.

EXAMPLE 6

(±)-3,3aβ,4,5,6,6aβ-hexahydro-4β-hydroxymethyl-5α-hydroxy-2H-cyclopenta[b]furane-2-on-formaldehyde acetal (compound of the formula IX, wherein $R^5$ and $R^6$ is hydrogen)

1 g. (5.88 mmoles) of lactone diol of the formula Id and 1 g. of paraformaldehyde are shaken in 20 ml. of benzene and then some drops of boron trifluoride etherate are added. The flask is closed and allowed to stand at room temperature for 4 days. After 4 days the reaction mixture is neutralized with triethyl amine, the precipitated salt is filtered off, the solvent is evaporated and the remaining oil is recrystallized from an ether/hexane mixture. The title compound is obtained.
$R_f = 0.37$ (ethyl acetate).

EXAMPLE 7

(±)-3,3aβ,4,5,6,6aβ-hexahydro-4β-hydroxymethyl-5α-hydroxy-2H-cyclopenta[b]furane-2-on-benzaldehyde-acetal (compound of the formula IX, wherein $R^5$ is phenyl and $R^6$ is hydrogen).

722 mg. (2.71 mmoles) of the racemic lactone diol diacetate of the formula Ic in 5 ml. of benzene are combined with the solution of 455 mg. (2.99 mmoles) of benzaldehyde diacetal in 4 ml. of benzene and the solution of 5 mg. of concentrated sulphuric acid in 0.2 ml. of methanol is added to the reaction mixture. The reaction mixture is heated for 15 to 20 hours and the methyl acetate is distilled off continuously. When the reaction is completed the mixture is neutralized with triethyl amine, the precipitated salt is filtered off and the filtrate is evaporated. The residue is dissolved in 10 ml. of absolute ether and crystallized upon addition of petroleum ether. The named compound is obtained. $R_f = 0.51$ (ethyl acetate).

EXAMPLE 8

(±)-3,3aβ,4,5,6,6aβ-hexahydro-4β-hydroxymethyl-5α-hydroxy-2H-cyclopenta[b]furan-2-on-acetone acetal (compound of the formula IX, wherein $R^5$ and $R^6$ is methyl)

To 102 mg. (0.56 mmoles) of the lactone diol of the formula Id in 10 ml. of benzene 2 ml. of 2,2-dimethoxy-propane (acetone-dimethylacetal) and 25 mg. of p-toluene-sulphonic acid monohydrate are added. The reaction mixture is kept at 75° to 80° C allowing the aseotropic mixture to distill off but keeping back the acetone/dimethyl acetal. After 9-10 hours the reaction is completed. Upon evaporating the reaction mixture a dark-red oil is obtained, which is dissolved in 5 ml. of ether, then crystallized upon the addition of 5 ml. of petroleum ether. 57. mg. of title compound are obtained.
$R_f = 0.50$ (on a $GF_{254}$ "Kieselgel nach Stahl" plate, with ethyl acetate).

EXAMPLE 9

(±)-3,3aβ,4,5,6,6aβ,7-hexahydro-4β-hydroxymethyl-5α-hydroxy-2H-cyclopenta[b]furane-2-on (compound of the formula Id)

to 9 ml. of a 36 to 38 percent aqueous formaldehyde solution 1 ml. of concentrated sulphuric acid is added with stirring, under cooling, in small portions, whereupon 1 g. (8.0 mmoles) of (±)-3,3aβ,6,6aβ-tetrahydro-2H-cyclopentano[b]furane-2-on is added to the mixture. The flask containing the reaction mixture is closed and kept at 70° C for 70 to 80 hours. The resulted yellowish-brown oily substance is poured onto 3 g. of sodium carbonate after opening the flask, and the suspension is thoroughly extracted with ethyl acetate. The combined ethyl acetate exctractions are washed with brine, dried over sodium sulphate, then the ethyl acetate is evaporated. The remaining yellow oil contains as a main component the lactone diol of the formula Id accompanied by a compound of the formula IX, in which $R^5$ and $R^6$ is hydrogen and by several not identified side products.

The compond of the formula Id is isolated by column chromatography as described in Example 3. The physical properties of the obtained racemic compound of the formula Id are identical with those of the (−)-enantiomer diol obtained in Example 3, except the melting point. The melting point of the racemic product is 91° to 92° C.

What we claim is:

1. A compound of the formula:

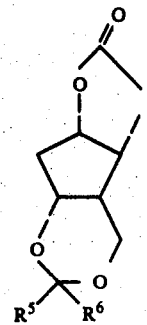

wherein $R^5$ and $R^6$ are selected from the group consisting of hydrogen, methyl and phenyl with the proviso that when one of $R^5$ and $R^6$ is phenyl, the other must be hydrogen.

2. (±)-3,3aβ,4,5,6,6aβ-hexahydro-4β-hydroxymethyl-5a-hydroxy-2H-cyclopenta[b]furane-2-on-formaldehyde acetal or an optically active (±) or (−) antipode thereof.

3. (±)-3,3aβ,4,5,6,6aβ-hexahydro-4-β-hydroxymethyl-5a-hydroxy-2H-cyclopenta[b]furane-2-on-acetoneacetal or an optically active (±) or (−) antipode thereof.

4. (±)-3,3aβ,4,5,6,6aβ-hexahydro-4-β-hydroxymethyl-5a-hydroxy-2H-cyclopenta[b]furane-2-on-benzaldehyde acetal or an optically active (±) or (−) antipode thereof.

* * * * *

UNITED STATES PATENT AND TRADEMARK OFFICE
CERTIFICATE OF CORRECTION

PATENT NO. : 4,126,622
DATED : 21 November 1978
INVENTOR(S) : TOMÖSKÖZI et al.

It is certified that error appears in the above—identified patent and that said Letters Patent are hereby corrected as shown below:

For the formula of Claim 1 (Col. 18, lines 1 - 14) read:

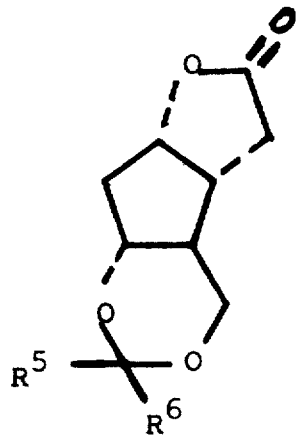

Signed and Sealed this

Twenty-ninth Day of May 1979

[SEAL]

Attest:

RUTH C. MASON
Attesting Officer

DONALD W. BANNER
Commissioner of Patents and Trademarks